(12) United States Patent  (10) Patent No.: US 6,347,939 B2
Abels                     (45) Date of Patent: *Feb. 19, 2002

(54) SELF-LIGATING ORTHODONTIC BRACKET

(76) Inventor: Norbert Abels, Alleestr. 30 A, 66424 Homburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/840,770

(22) Filed: Apr. 23, 2001

Related U.S. Application Data

(63) Continuation of application No. 09/424,102, filed as application No. PCT/EP99/01814 on Mar. 18, 1999, now Pat. No. 6,220,857.

(30) Foreign Application Priority Data

Mar. 19, 1998 (DE) .......................... 198 12 184

(51) Int. Cl.⁷ .................................................. A61C 7/12
(52) U.S. Cl. .............................................. 433/10; 433/8
(58) Field of Search ........................... 433/8, 9, 10, 11, 433/13, 22

(56) References Cited

U.S. PATENT DOCUMENTS

| 2,011,575 A | 8/1935  | Ford     |
| 3,128,552 A | 4/1964  | Broussard |
| 3,748,740 A | 7/1973  | Wildman  |
| 3,854,207 A | 12/1974 | Wildman  |
| 4,077,126 A | 3/1978  | Pletcher |
| 4,103,423 A | 8/1978  | Kessel   |
| 4,144,642 A | 3/1979  | Wallshein |
| 4,171,568 A | 10/1979 | Förster  |
| 4,180,912 A | 1/1980  | Kesling  |
| 4,279,593 A | 7/1981  | Röhlcke  |
| 4,371,337 A | 2/1983  | Pletcher |
| 4,419,078 A | 12/1983 | Pletcher |
| 4,492,573 A | 1/1985  | Hanson   |
| 4,512,740 A | 4/1985  | Kurz     |
| 4,527,975 A | 7/1985  | Ghafari et al. |
| 4,559,012 A | 12/1985 | Pletcher |
| 4,559,013 A | 12/1985 | Amstutz et al. |
| 4,597,739 A | 7/1986  | Rosenberg |
| 4,614,497 A | 9/1986  | Kurz     |
| 4,634,662 A | 1/1987  | Rosenberg |
| 4,655,708 A | 4/1987  | Fujita   |
| 4,687,441 A | 8/1987  | Klepacki |
| 4,698,017 A | 10/1987 | Hanson   |
| 4,712,999 A | 12/1987 | Rosenberg |
| 4,786,252 A | 11/1988 | Fujita   |
| 4,846,681 A | 7/1989  | Mourany et al. |
| 4,850,865 A | 7/1989  | Napolitano |
| 4,913,654 A | 4/1990  | Morgan et al. |
| 5,037,296 A | 8/1991  | Karwoski |
| 5,062,794 A | 11/1991 | Miura    |
| 5,078,596 A | 1/1992  | Carberry et al. |
| 5,094,614 A | 3/1992  | Wildman  |
| 5,125,832 A | 6/1992  | Kesling  |
| 5,160,260 A | 11/1992 | Chang    |

(List continued on next page.)

FOREIGN PATENT DOCUMENTS

| DE | 1 184 451    | 12/1964 |
| DE | 23 57 573    | 5/1975  |
| DE | G 91 12 872.2 | 3/1992 |
| DE | 296 08 349 U1 | 11/1996 |
| EP | 0 714 639 A2 | 6/1996  |
| WO | WO 94/00072  | 1/1994  |
| WO | WO 00/33760  | 6/2000  |

OTHER PUBLICATIONS

Konstruieren mit Kunststoffen, Gunter Erhard, Carl Hanser Verlag München Wien, pp. 314–329, 1999.

Primary Examiner—Ralph A. Lewis
(74) Attorney, Agent, or Firm—Workman, Nydegger & Seeley

(57) ABSTRACT

An orthodontic securing element has a base (1) and at least one holder (3, 4) which is arranged on the base (1). A covering (2) which covers over the base (1) and the holder (3, 4) is secured to the base (1).

13 Claims, 3 Drawing Sheets

U.S. PATENT DOCUMENTS

| | | | |
|---|---|---|---|
| 5,161,969 | A | 11/1992 | Pospisil et al. |
| 5,174,754 | A | 12/1992 | Meritt |
| 5,224,858 | A | 7/1993 | Hanson |
| 5,275,557 | A | 1/1994 | Damon |
| 5,322,435 | A | 6/1994 | Pletcher |
| 5,344,315 | A | 9/1994 | Hanson |
| 5,356,288 | A | 10/1994 | Cohen |
| 5,380,197 | A | 1/1995 | Hanson |
| 5,456,599 | A | 10/1995 | Hanson |
| 5,470,228 | A | 11/1995 | Franseen et al. |
| 5,474,445 | A | 12/1995 | Voudouris |
| 5,474,446 | A | 12/1995 | Wildman et al. |
| 5,556,276 | A | 9/1996 | Roman et al. |
| 5,562,444 | A | 10/1996 | Heiser et al. |
| 5,586,882 | A | 12/1996 | Hanson |
| 5,630,715 | A | 5/1997 | Voudouris |
| 5,630,716 | A | 5/1997 | Hanson |
| 5,685,711 | A | 11/1997 | Hanson |
| 5,711,666 | A | 1/1998 | Hanson |
| 5,738,513 | A | 4/1998 | Hermann |
| 5,857,849 | A | 1/1999 | Kurz |
| 5,863,199 | A | 1/1999 | Wildman |
| 5,885,074 | A | 3/1999 | Hanson |
| 5,906,486 | A | 5/1999 | Hanson |
| D412,363 | S | 7/1999 | Stevens |
| D412,579 | S | 8/1999 | Stevens |
| D412,988 | S | 8/1999 | Stevens |
| 5,938,435 | A | 8/1999 | Raspino, Jr. |
| 5,964,589 | A | 10/1999 | Musich |
| 6,017,118 | A | 1/2000 | Gasvoda et al. |
| 6,042,373 | A | 3/2000 | Hermann |
| 6,042,374 | A | 3/2000 | Farzin-Nia et al. |
| 6,071,119 | A | 6/2000 | Christoff et al. |
| 6,220,857 | B1 * | 4/2001 | Abels ............ 433/8 |

* cited by examiner

SELF-LIGATING ORTHODONTIC BRACKET

This application is a continuation of U.S. application Ser. No. 09/424,102, filed Dec. 21, 1999, now U.S. Pat. No. 6,220,857, which is a 371, of PCT/EP99/01814, field Mar. 18, 1999, which is incorporated herein in its entirety by reference.

BACKGROUND OF THE INVENTION

1. Field of Invention

The present invention relates to an orthodontic securing element for orthodontic therapy, which is also called a bracket.

2. Related Technology

A large number of juvenile and adult patients are treated orthodontically for correcting existing dysgnathias. In order to achieve the goal of the treatment as rapidly as possible and to the full extent planned, and also in order to be less dependent on the cooperation of the patient and to realize somatic tooth movements, firmly seated orthodontic apparatuses are in use.

The disadvantages of firmly seated apparatuses of this kind, such as brackets and bands, are a substantially more difficult oral hygiene (removal of calcium in the region of the brackets) and also a significantly reduced wearing comfort which is caused by the brackets which have been used up to now. Food residues remain around the brackets with bacterial settlement (plaque lawn and subsequent formation of caries) as a result, with the acids thereby arising causing decalcinations of the hard tooth substances, which leads as a result to destruction of the hard tooth substance. In addition mouth odors, the presence of which is very disagreeable for the patients wearing the apparatus, arise through the bacterial settlement and through the decomposing food residues. In addition conventional brackets have proved disadvantageous in so far as they offer an insufficient wearing comfort, can cause injuries to the lips, tongue and cheeks and negatively influence the lingual technique.

SUMMARY OF THE INVENTION

The problem (object) on which the invention is based is to create an orthodontic securing element (bracket) which has a greater wearing comfort.

This object is satisfied through an orthodontic securing element having a base and at least one holder which is arranged on the base, with a cover which covers over the base and the holder being secured to the base.

In accordance with the invention a preferably hood-like cover is placed onto the entire bracket so that the previously used parts of the holder, which have edges, are covered. Through this the required parts of the holder, for example slots, bracket wings, hooks and the like are hidden beneath the cover so that lips, cheeks or the tongue are not injured or irritated by these elements. Through a smooth and arched execution of the cover the self cleaning mechanism of the teeth is in addition substantially less impaired.

A further advantage of the complete covering of the securing element in accordance with the invention lies in the lower susceptibility to bacterial contamination. Through the covering in accordance with the invention all angles, edges and niches of the securing element or of its holder respectively are covered over with respect to the oral cavity so that no food residues can become fixed there and a bacterial attack is significantly reduced.

Advantageous further developments of the invention are described in the description, in the drawings and in the subordinate claims.

In accordance with a first advantageous embodiment the contour of the edge of the covering corresponds to the outer contour of the base of the securing element. Thus in this embodiment the entire bracket is substantially completely covered over by the covering so that the wearing comfort is optimized.

The covering is preferably executed to be hood-like and has no disturbing corners or edges. In this a convex curvature with radii of curvature which are as large as possible is preferred, since a shape of this kind is felt to be the least disturbing. Through a continuously arched surface both the bacterial attack and the irritation of the oral cavity are minimized.

The covering is preferably closed with the exception of two openings for passing a bow through, with the openings preferably being matched to the cross-section of the bow. Thus in this embodiment as well it is ensured that no food residues can penetrate under the covering in the region of the openings through which the bow is passed.

In order to enable a simple placing on of the covering onto the bracket with a bow secured thereto, the covering can in an advantageous manner be formed to be slit in the region of the openings. Through this the covering, which is preferably manufactured of an elastic material, can be briefly opened in the region of the slits so that the covering can be placed onto the base, with it being possible for the bow after being placed on to emerge through the openings which are provided. After the placing on the covering closes as a result of its elastic properties so that the bracket is completely protected in the direction of the oral cavity.

In accordance with a further advantageous embodiment of the invention the base has at its outer periphery a circumferential ledge, onto which the covering can be placed on. In this way the transition between the outer surface of the covering and the tooth surface can be formed without edges, with a good sealing between the base and the covering being ensured at the same time.

The base preferably has rounded off corners or is executed substantially ovally or elliptically respectively. Through a shaping of this kind disturbing corners or edges are also avoided in the region of the base, which further increases the wearing comfort.

The covering can be foldably secured to the base or be placeable onto the base, for example through a clamping seating. It is also possible to secure the covering through adhesive bonding.

In order to facilitate a measurement of the bracket position with a camera and a computer system, one or more registering aid devices can furthermore be arranged within the covering, for example at the holder, which are used as reference points.

In accordance with a further advantageous embodiment of the invention one or more hooks are arranged at the securing element which are likewise protected by the covering. In order for example to move teeth in a specific direction, these hooks can be folded out in accordance with the invention so that they project beyond the outer contour of the base and are easy to reach there. The hooks likewise have a rounded off and thus non disturbing outer contour. After the desired moving of the teeth the hooks can be moved back again so that the covering can be placed on onto the base.

In certain uses it can be advantageous to provide an additional opening for the passage through of the hook. This opening can for example be formed by a punched part which is broken out only when required. A renewed closing, for example through pivotal connection with the help of a film hinge or the like is also possible. In this case the hook can be used without it being necessary for the covering to be taken off.

In order to enable a rigid connection between palate bows and for example two premolars each as anchoring teeth, a connection mechanism between the palate bow and the bracket is provided in accordance with a further embodiment. Furthermore, a slit, which is also called a slot, and which serves for receiving the bow, is provided within the bracket. This slot has a reversible, individually insertable holding mechanism for the bow, so that the most diverse of orthodontic anchoring tasks can be solved.

In accordance with a further aspect of the present invention at least the outer surface of the covering has self cleaning properties, which has not previously been used in dental medicine for brackets. Self cleaning materials are known in principle and have a self cleaning effect which exploits the so-called "lotus effect" and which is achieved through a surface with a predetermined roughness. Through this preset roughness, polar and nonpolar liquids can run off the surface in droplets, without residues, with contamination particles being taken along in the process (cf. C. Neinhuis and W. Barthlott, 1997: Characterization and distribution of water-repellent, self cleaning plant surfaces. Annals of Botany 79).

The self cleaning properties can preferably be achieved through an anti adhesion coating, for example of a sol-gel material. Sol-gel materials of this kind can be manufactured by a wet chemical method in which, starting from a liquid colloid-disperse system a reaction is initiated which leads to the build-upof a three dimensional network. For example silicic acid esters or metal alkoxides, which react through hydrolysis and condensation to form an inorganic network, can be used as starting compounds. Through this, repellent surfaces can be produced which have the desired self cleaning properties.

Preferably, not only the outer surface of the covering, but also the entire securing element is provided with an anti adhesive coating, with it not being necessary to equip the lower side of the base, which is secured at a tooth, with a coating of this kind.

In accordance with a further aspect of the present invention, storage locations for bacteriostatic and/or bactericidal substances are provided at the securing element and inside the covering. Gels or pastes with bacteriostatic or bactericidal action can be introduced into these storage locations, for example cavities. Silver-fluorine compounds, phenol compounds and the like come under consideration as bactericidal substances.

The present invention relates not only to an orthodontic securing element, but also to the described covering, with which conventional brackets can be subsequently equipped.

BRIEF DESCRIPTION OF THE DRAWINGS

In the following the present invention will be explained in a purely exemplary manner with reference to the accompanying drawings and with reference to an advantageous embodiment. Shown are:

FIG. 2 the securing element of FIG. 1 with the covering placed on;

DETAILED DESCRIPTION OF THE PREFERRED EMBODIMENTS

Figure 1:
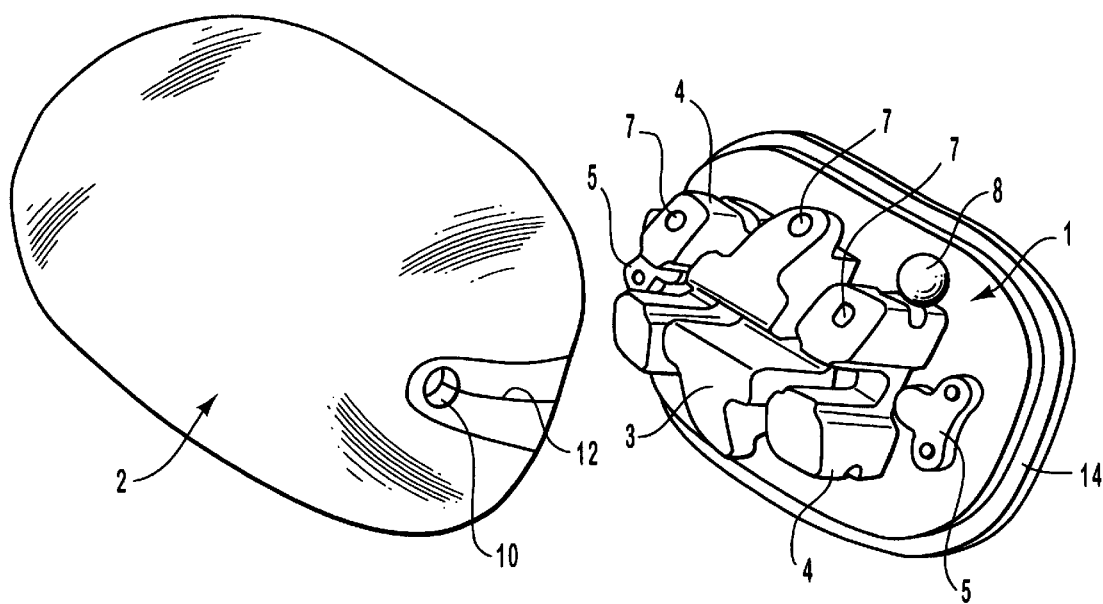
FIG. 1 a perspective illustration of a securing element with the associated covering.

The orthodontic securing element illustrated in the figures, also called a bracket, has a base 1 on which a holder for a bow is arranged. The holder has an insertable, reversible bow holder mechanism 3, 4 so that the most diverse of orthodontic anchoring tasks can be solved.

The base 1 is executed substantially rectangularly, but has strongly rounded off corners. At the two narrow sides of the base, an inner rotation wing 5 for the derotation of teeth is in each case secured on the former. Furthermore, a registering aid device 7 is arranged on each of the individual elements 3, 4 of the bow holder mechanism and enables a measurement using a camera and a computer system. Furthermore, at the element 4 of the bow holder mechanism at the right in FIG. 1 a hook 8 is provided which can be folded out in order to move teeth in a specific direction.

Figure 3:
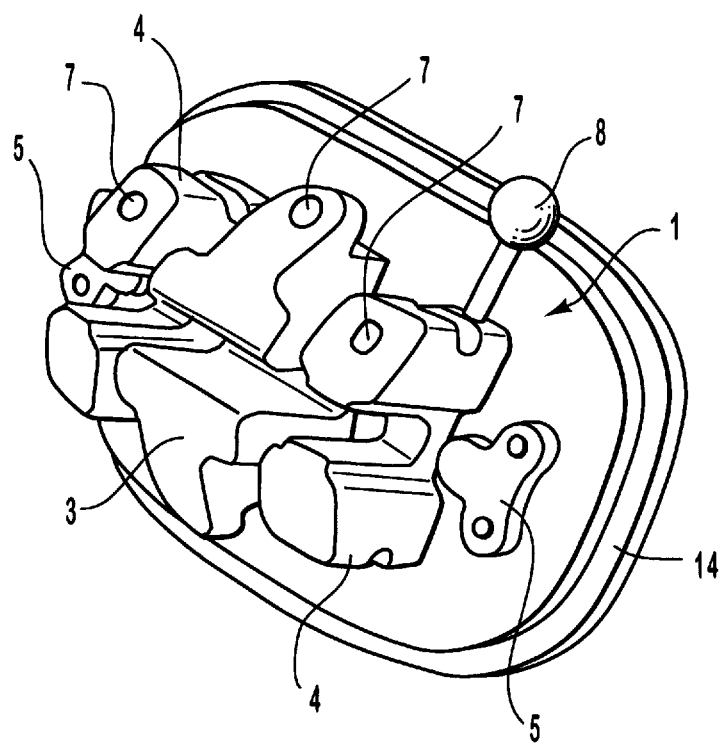
FIG. 3 the securing element of FIG. 1 without the covering and with drawn out hook.

FIG. 3 shows this hook 8 in the folded out state. In this position an intervention can be carried out at the hook in order to achieve a desired displacement of the teeth. As FIG. 3 further shows, the hook 8 projects with its sphere-like end beyond the outer contour of the base 1. In the folded in or pushed in state respectively the end of the hook 8 is located inside the outer contour of the base 1 (cf. FIG. 1).

As FIGS. 1 and 3 further show, a slit is formed through the bow holder mechanism 3, 4 which serves for the accommodation of the bow (not illustrated). In this the bow is inserted into the slit and arrested there.

FIG. 1 furthermore shows the covering 2 which is provided in accordance with the invention and which can be secured to the base 1. This covering 2 is manufactured of plastic and executed in the manner of a hood without disturbing corners or edges. The outer surface of the covering 2 always extends so as to be convexly arched, with the contour of the edge of the covering 2 corresponding to the outer contour of the base 1.

Figure 2:
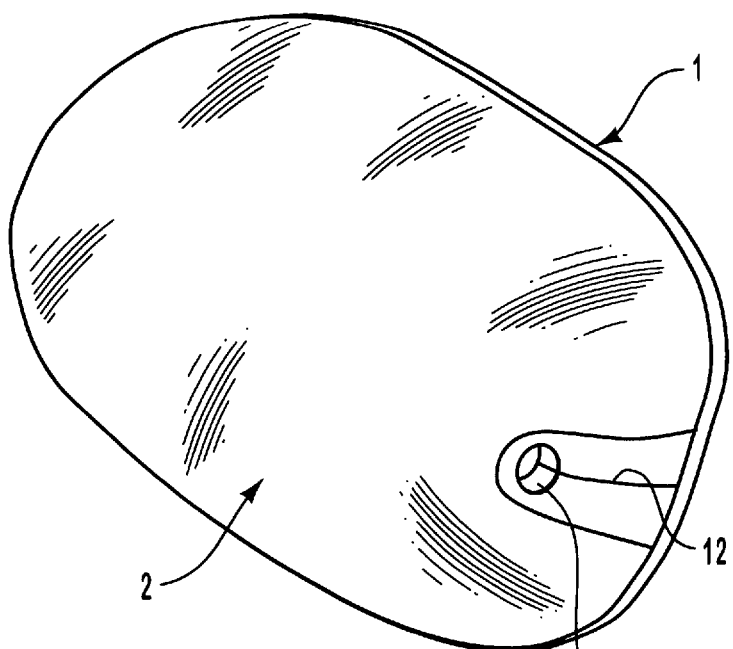

As FIG. 2 shows, the covering 2 is placed onto the base 1 and in this state completely covers over the base 1 and the holder 3, 4 which is mounted thereon as well as the rotation wings 5 and the hook 8 which can be folded in. In this state the space which is enclosed between the base 1 and the covering 2 is closed with the exception of two openings 10 (in FIGS. 1 and 2 only one opening can be recognized), which serve for passing the bow through. The two mutually oppositely lying openings 10 are arranged approximately centrally at the two narrow sides of the covering 2, with the cross-section of the openings 10 being matched to the cross-section of the bow. In order to enable a placing on of the covering 2 onto the base 1 when the bow is inserted into the securing element, the covering 2 is formed to be slit in the region of the openings 10. For this a slit 12 extends in each case rectilinearly from the opening 10 at right angles up to the outer edge of the covering 2. As a result of the elastic execution of the plastic covering 2 the slit 12 is normally closed. The latter can however be opened through a gentle pushing apart of the longitudinal sides of the covering when placing on the covering 2 so that the bow can be passed through the slit 12 into the opening 10. Then the slit 12 closes up again, through which at the same time the covering 2 is held on the base 1 by the bow.

As FIGS. 1 to 3 further show, the base 1 has at its outer periphery a circumferential ledge 14, onto which the outer edge of the covering 2 is placed. In the placed on state the transition between the outer surface of the covering 2 and the tooth surface is free from edges, which means that the outer surface of the covering 2 merges continuously and smoothly into the outer end side of the ledge 14.

Figure 4:
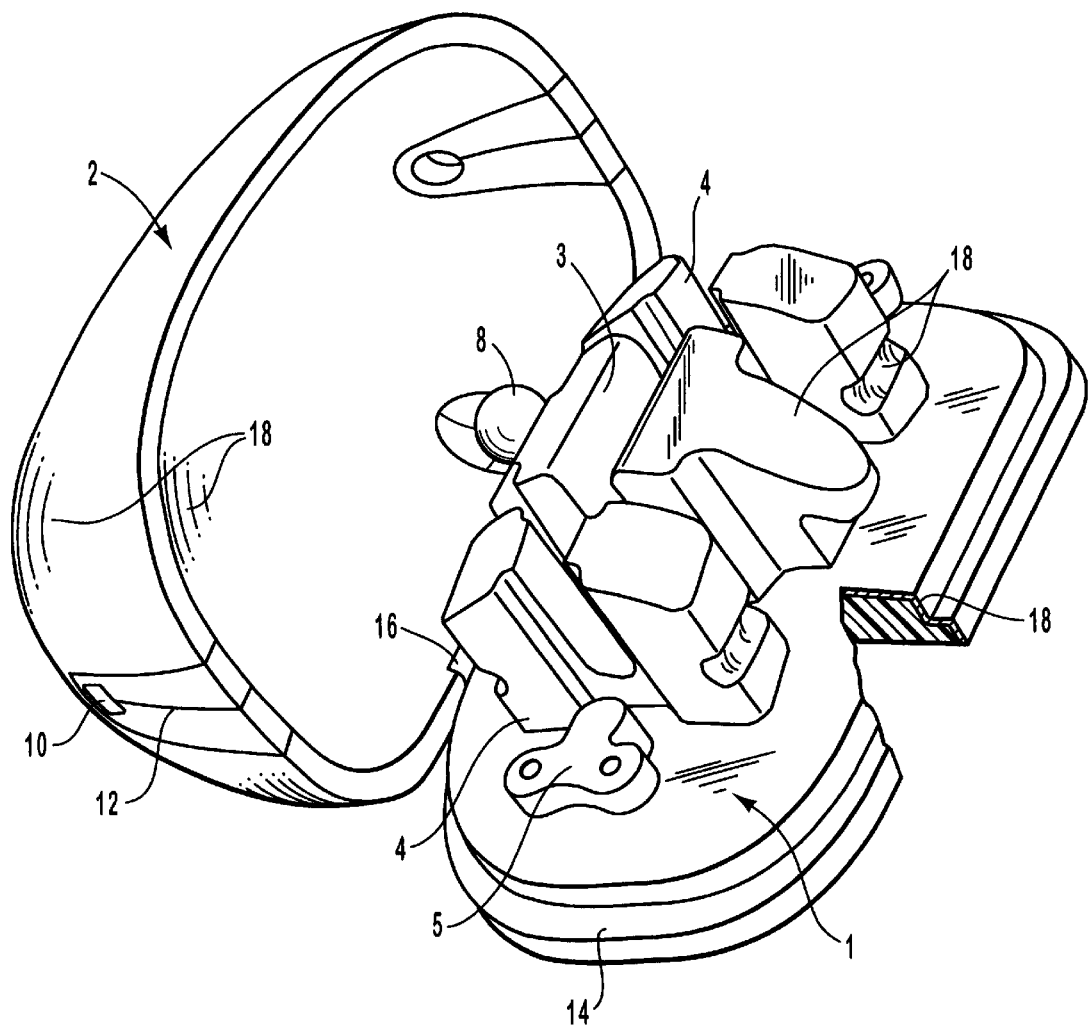
FIG. 4 the securing element of FIG. 1 with a hingedly secured cover.

All elements of the securing element in accordance with the invention are provided with an anti adhesion coating 18 which has self cleaning properties (see FIG. 4). Furthermnore, storage locations for bacteriostatic and/or bactericidal substances are provided at the securing element and inside the covering. Storage locations of this kind (not illustrated) can for example be provided in the form of depressions or cavities.

In addition to the illustrated exemplary embodiment it is also possible that the covering also completely covers over the base at its outer edge. Furthermore, as seen in FIG. 4 the cover 2 may be secured by a hinge 16 to the base 1.

It should again be emphasized that the present invention is not restricted to a securing element, but also comprises a covering which is suitable for a subsequent equipping of conventional brackets.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An orthodontic bracket for orthodontic therapy comprising:
    a base having a circumferential ledge;
    a holder for a bow arranged on said base; and
    a cover separate from and hingedly connected to said base by a hinge element comprising a flexible strip, wherein said cover is selectively rotated about said hinge so as to selectively cover and uncover said holder and at least a portion of said base, said cover having a generally curved outer surface and an edge configured so as to generally correspond to and rest upon said circumferential ledge when said cover is in a closed position.

2. An orthodontic bracket as defined in claim 1, wherein said edge of said cover generally corresponding to an outer contour of said base.

3. An orthodontic bracket as defined in claim 1, further including at least one registering aid arranged at said holder for facilitating an optical measurement.

4. An orthodontic bracket as defined in claim 1, wherein said holder further includes at least one hook that is movable beyond an outer contour of the base.

5. An orthodontic bracket as defined in claim 1, wherein said cover includes an opening through which said hook can selectively extend while said cover is in a closed position relative to said base.

6. An orthodontic bracket as defined in claim 5, wherein said opening, is renewable as a result of a film hinge within said cover.

7. An orthodontic bracket as defined in claim 1, further including a connection mechanism for securing at a palate bow.

8. An orthodontic bracket as defined in claim 1, wherein at least the outer surface of said cover has self-cleaning properties and has an anti-adhesion coating of a sol-gel material.

9. An orthodontic bracket as defined in claim 1, wherein a substantial portion of the orthodontic bracket has an anti-adhesion coating.

10. An orthodontic bracket as defined in claim 1, wherein said cover includes storage locations for at least one of a bacteriostatic or bactericidal substance.

11. An orthodontic bracket as defined in claim 1, wherein said cover comprises plastic.

12. An orthodontic bracket for orthodontic therapy comprising:
    a base adapted to receive a bow;
    a cover, separate from said base, having a generally curved outer surface and being configured so as to substantially cover said base when in a closed position relative to said base; and
    a hinge element comprising a flexible strip interconnecting said base and said cover about which said cover is selectively rotated between said closed position and an open position in which said base is at least partially uncovered.

13. An orthodontic bracket for orthodontic therapy comprising:
    a base adapted to receive a bow;
    a plastic cover, separate from said base, having a generally curved outer Surface and being configured so as to substantially cover said base when in a closed position relative to said base and
    a hinge element comprising a flexible strip interconnecting said base and said cover about which sa id cover is selectively rotated between said closed position and an open position in which said base is at least partially uncovered.

* * * * *

UNITED STATES PATENT AND TRADEMARK OFFICE
CERTIFICATE OF CORRECTION

PATENT NO.    : 6,347,939
DATED         : February 19, 2002
INVENTOR(S)   : Norbert Abels It is certified that error appears in the above-identified patent and that said Letters Patent is hereby corrected as shown below:

Column 1,
Line 3, change "field" to -- filed --

Column 5,
Line 4, change "Furthermnore" to -- Furthermore --
Line 43, change "sa id" to -- said --

Signed and Sealed this

Twenty-first Day of May, 2002

Attest:

JAMES E. ROGAN
*Attesting Officer*   *Director of the United States Patent and Trademark Office*